US011141307B2

United States Patent
Doreswamy et al.

(10) Patent No.: US 11,141,307 B2
(45) Date of Patent: Oct. 12, 2021

(54) DEVICE, SYSTEM AND APPARATUS FOR FEMALE URINE COLLECTION

(71) Applicant: Gokula Education Foundation (Medical), Bangalore (IN)

(72) Inventors: Venkatesh Doreswamy, Bangalore (IN); Medha Yogish Rao, Bangalore (IN); Arun Kumar Mohan, Bangalore (IN); Jolly Anil John, Bangalore (IN); Surendra Rao Shankapal, Bangalore (IN); Dakshath P Jembige, Bangalore (IN); Nagaraja Basavaraja Setty, Bangalore (IN)

( * ) Notice: Subject to any disclaimer, the term of this patent is extended or adjusted under 35 U.S.C. 154(b) by 495 days.

(21) Appl. No.: 16/016,675

(22) Filed: Jun. 25, 2018

(65) Prior Publication Data

US 2019/0240063 A1    Aug. 8, 2019

(30) Foreign Application Priority Data

Feb. 5, 2018    (IN) .............................. 201841004344

(51) Int. Cl.
*A61F 5/455*    (2006.01)
*A61F 5/44*    (2006.01)

(52) U.S. Cl.
CPC .......... *A61F 5/4553* (2013.01); *A61F 5/4408* (2013.01)

(58) Field of Classification Search
CPC ........ A61F 5/4553; A61F 5/455; A61F 5/451; A61F 5/4556; A61M 25/10; E03D 13/00
See application file for complete search history.

(56) References Cited

U.S. PATENT DOCUMENTS

| | | | | |
|---|---|---|---|---|
| 4,681,572 A | * | 7/1987 | Tokarz | A61B 1/307 600/574 |
| 5,004,463 A | * | 4/1991 | Nigay | A61F 5/455 604/329 |
| 5,147,301 A | * | 9/1992 | Ruvio | A61F 5/451 600/29 |
| 6,342,049 B1 | * | 1/2002 | Nichols | A61F 5/4553 604/327 |
| 7,398,565 B1 | * | 7/2008 | Chou | E03D 13/005 4/300.3 |
| 2001/0037098 A1 | * | 11/2001 | Snyder | A61F 5/4553 604/331 |
| 2006/0155214 A1 | * | 7/2006 | Wightman | A61F 5/455 600/574 |

(Continued)

*Primary Examiner* — Adam Marcetich
*Assistant Examiner* — Meagan Ngo

(57) ABSTRACT

A non-invasive female urine collection device comprising a first pipe with an inflatable balloon attached to a first end of the first pipe; and a urine collection member attached to a second end of the first pipe such that, when the first end of the first pipe is inserted into vagina, the urine collection member covers urethra for collecting the urine discharged through the urethra. The urine collection member further comprising a first membrane and a second membrane together forming a urine collection pouch, in that the second membrane is shorter than the first membrane exposing the first membrane around Urethra for collecting the urine discharged through the urethra. The urine collection member further comprising a set of spikes formed on the first membrane in line with the urethra to prevent splashing of urine coming out of urethra.

7 Claims, 13 Drawing Sheets

(56) References Cited

U.S. PATENT DOCUMENTS

| | | | |
|---|---|---|---|
| 2011/0028922 A1* | 2/2011 | Kay | A61F 5/4553 604/329 |
| 2015/0305917 A1* | 10/2015 | Su | A61F 5/451 4/144.1 |
| 2018/0200101 A1* | 7/2018 | Su | A61F 5/4405 |

* cited by examiner

Application No. 16/016,675
Amdt. Dated Dec. 28, 2020
Reply to Final Office action of
Sept. 29, 2020
Replacement Sheet

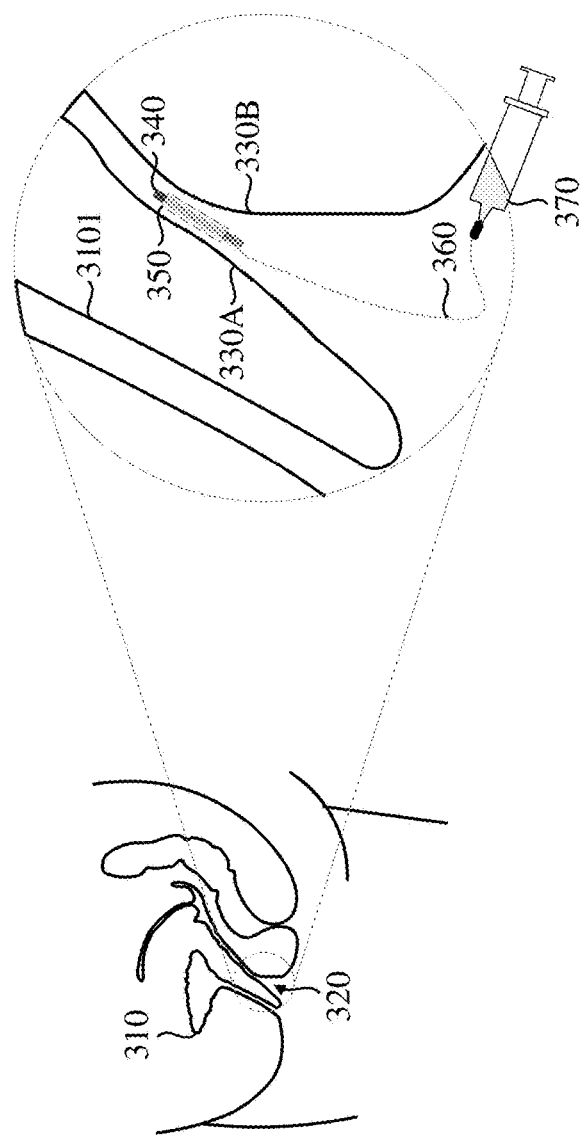

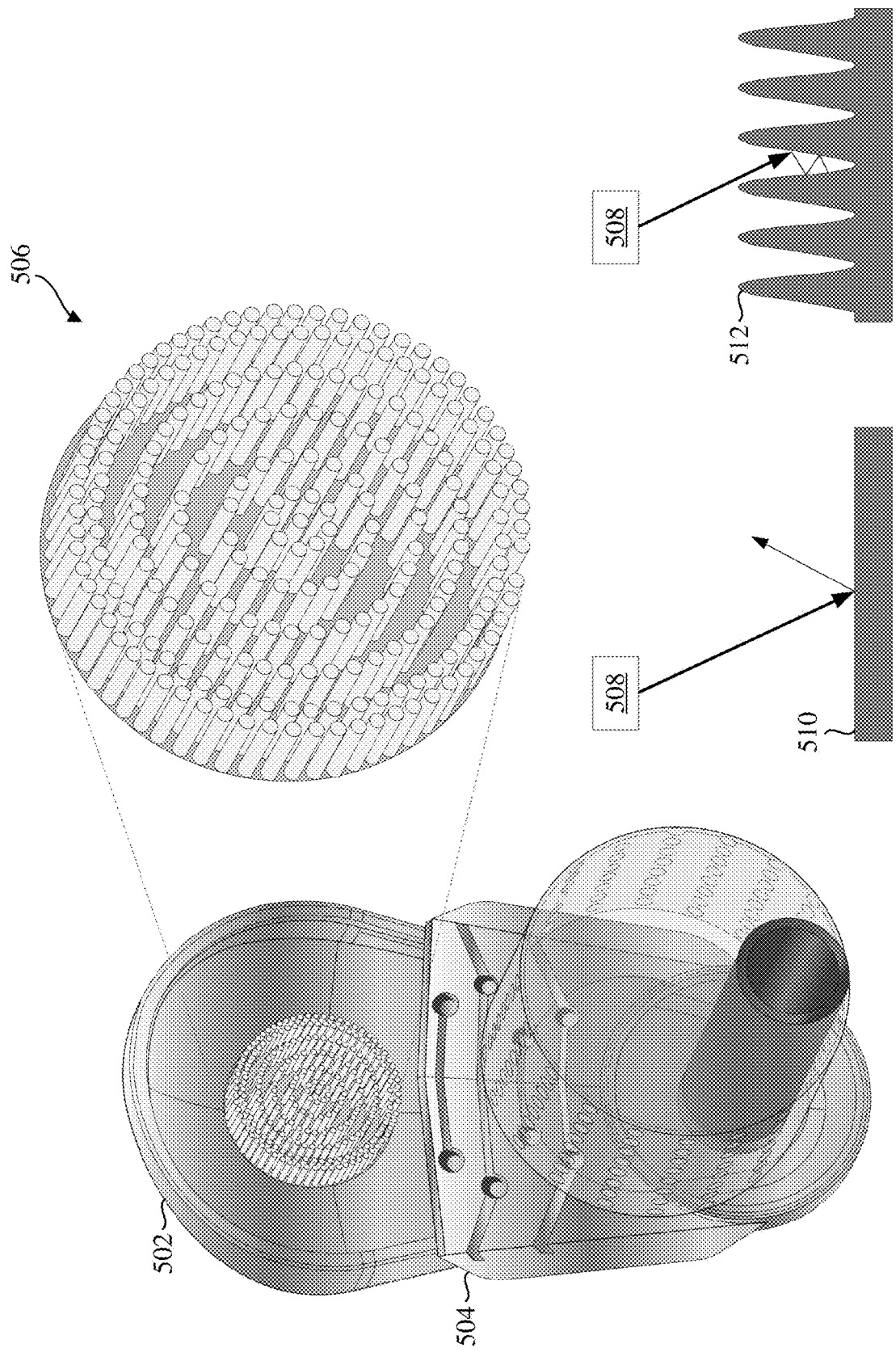

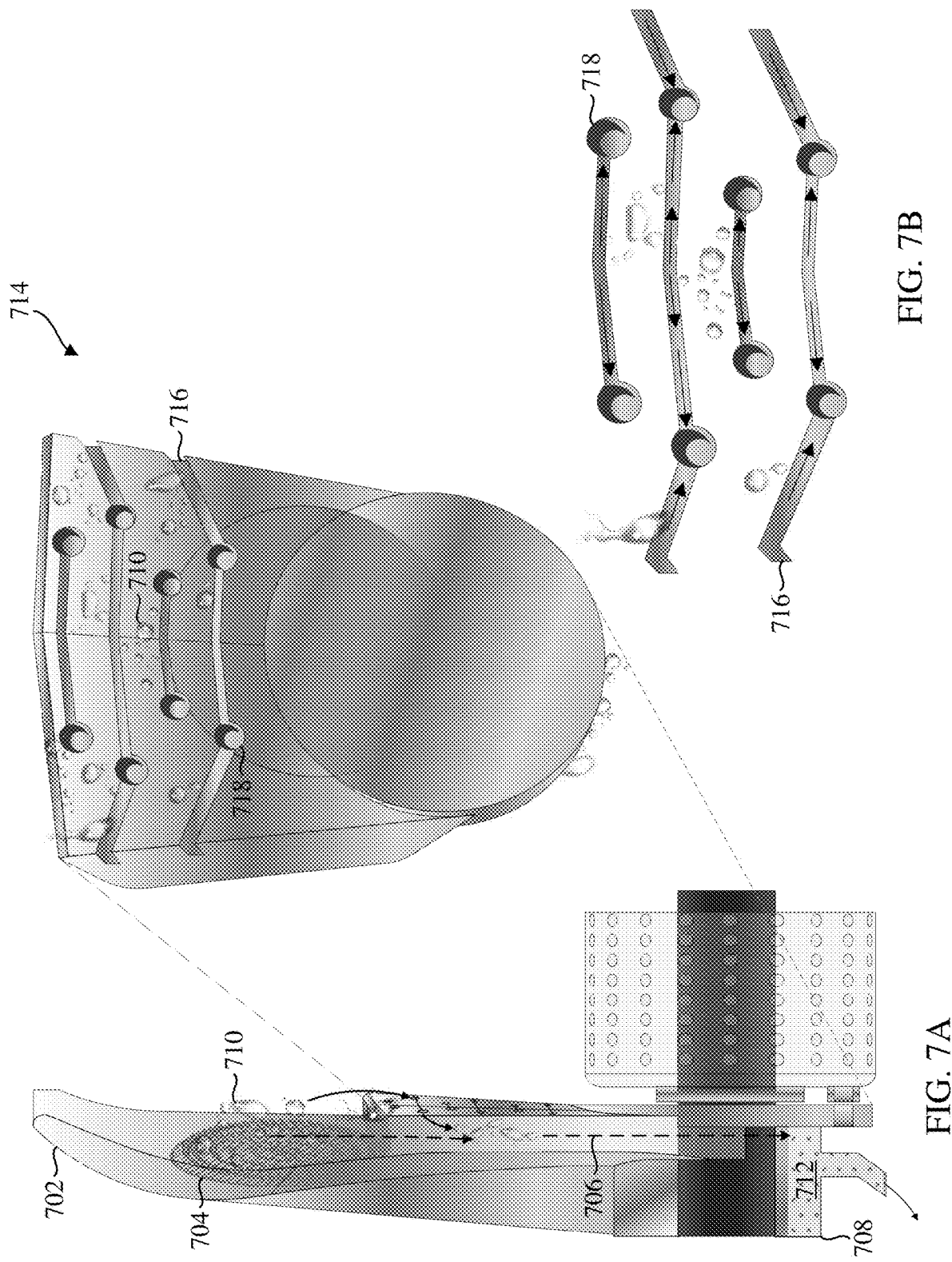

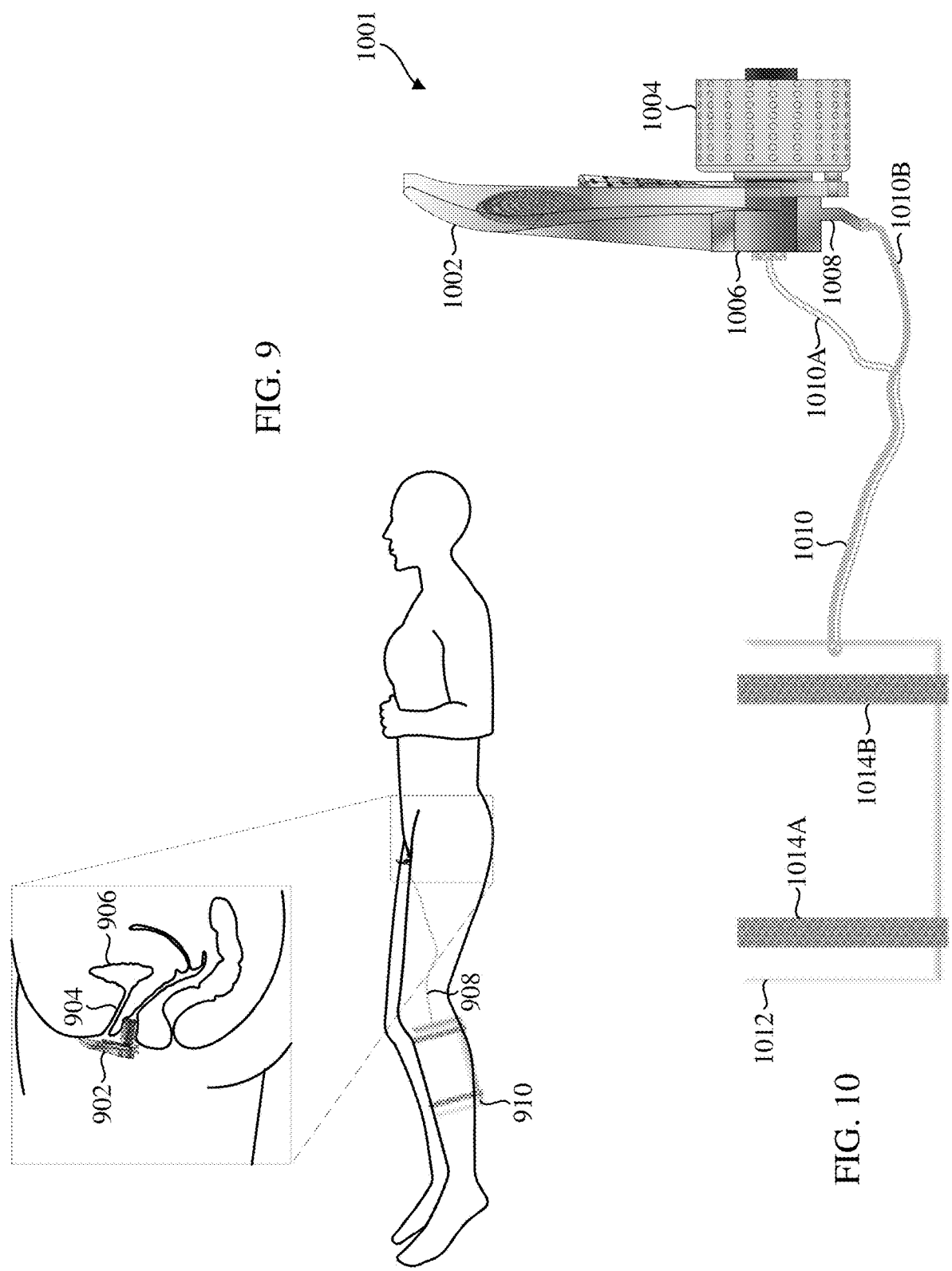

DEVICE, SYSTEM AND APPARATUS FOR FEMALE URINE COLLECTION

CROSS REFERENCES TO RELATED APPLICATIONS

This application claims priority from Indian patent application No. 201841004344 filed on Feb. 5, 2018 which is incorporated herein in its entirety by reference.

BACKGROUND

Field of Invention

Embodiments of the present disclosure relate generally to a medical device and more specifically to a non-invasive device, system and apparatus for female urine collection to avoid infections while in coma or in supine condition.

Related Art

Involuntary discharge of urine (urinary incontinence) is one of the major concern and a common problem in females who are not able to control their bladder at the time of pregnancy, childbirth, and menopause but not limited to those confined to bed by serious trauma and severe illness.

In order to manage the involuntary discharge of urine in females, various medications and drugs are being used which are proved to be ineffective in solving this problem. Conventionally, medical experts are using various devices for managing the urinary incontinence by inserting/fixing them into bladder through urethra. These devices are uncomfortable to use and their association with the bladder leads to urinary tract infections.

In recent days, various types of devices are developed by medical experts to control involuntary urinary discharge. However, they are bulky in size and few of them lack proper grip in holding the device in a firm position which makes them inefficient in aiding people with urinary incontinence. Also, proper care must be taken while using these devices as they severely affect mobility of a person using them and may cause more infections to the associated parts of the body.

The jet flow of urine coming out from urethra gets splashed and even outflows/leaks from the conventional devices causing more discomfort and creating more infections in and around the urethra region. Further, substantial variations in shape of organs around orifice of urethras in different females pose challenges in fixing conventional urine collection devices.

Besides inducing new urinary infections, the complexity in size and shape of conventional devices makes them ineffective and unable to use in specific conditions for example in a coma/supine condition. In few cases, conventional urine collection devices but not limited to wearable devices are responsible for causing lower back pain, chills/fever, swelling at insertion site and change in mental status of an individual.

SUMMARY

According to an aspect of the present disclosure, a non-invasive female urine collection device comprising a first pipe with an inflatable balloon attached to a first end of the first pipe; and a urine collection member attached to a second end of the first pipe such that, when the first end of the first pipe is inserted into vagina, the urine collection member covers urethra for collecting the urine discharged through the urethra. The urine collection member further comprising a first membrane and a second membrane together forming a urine collection pouch, in that the second membrane is shorter than the first membrane exposing the first membrane around Urethra for collecting the urine discharged through the urethra. The urine collection member further comprising a set of spikes formed on the first membrane in line with the urethra to prevent splashing of urine coming out of urethra.

Several aspects are described below, with reference to diagrams. It should be understood that numerous specific details, relationships, and methods are set forth to provide a full understanding of the present disclosure. One who skilled in the relevant art, however, will readily recognize that the present disclosure can be practiced without one or more of the specific details, or with other methods, etc. In other instances, well-known structures or operations are not shown in detail to avoid obscuring the features of the present disclosure.

BRIEF DESCRIPTION OF DRAWINGS

FIGS. 3A and 3B are the diagrams illustrating the manner in which a non-invasive female urine collecting device is anchored to vaginal region in an embodiment of the present disclosure.

FIG. 5A through 5C are the diagrams illustrating anti-splash cone spikes present in the non-invasive female urine collecting device of the present disclosure.

FIGS. 7A and 7B are the diagrams illustrating functionality of the non-invasive female urine collecting device in collecting urine from urethra in an embodiment of the present disclosure.

FIG. 9 illustrates an example implementation of the non-invasive female urine collecting device of the present disclosure while in coma/supine condition in an embodiment.

FIG. 10 is a sketch illustrating a urinary drainage bag coupled to the non-invasive female urine collecting device of the present disclosure for collecting urine and vaginal secretions in another embodiment.

DETAILED DESCRIPTION OF THE PREFERRED EXAMPLES

Figure 1A:
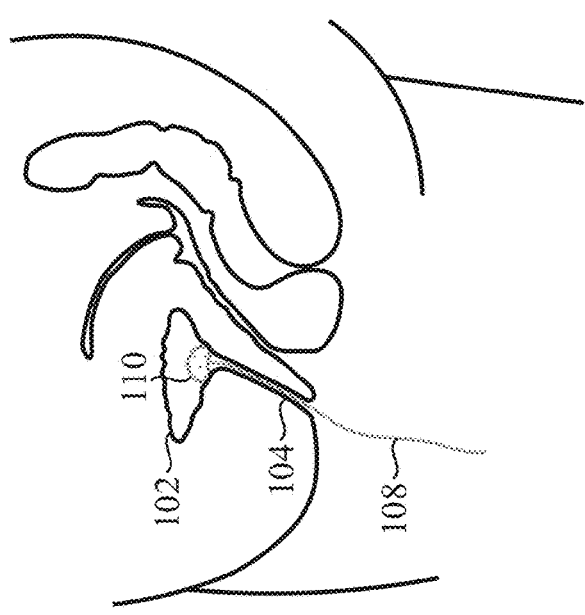
FIG. 1A through 1C are the diagrams illustrating an example indwelling urinary catheter used for urine collection in females with urinary incontinence.
Figure 1C:
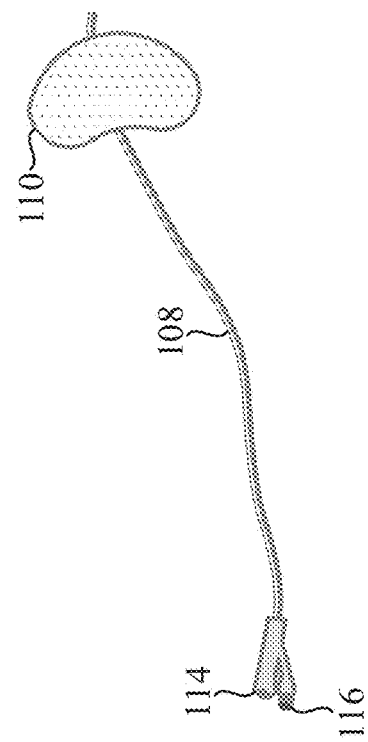
Figure 1B:
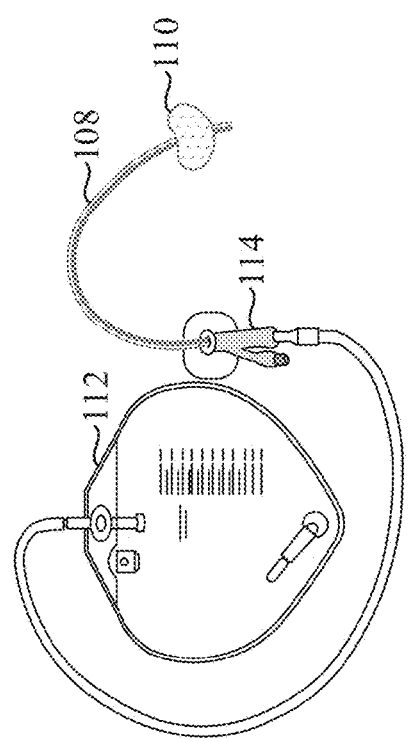

FIG. 1A through 1C are the diagrams illustrating an example indwelling urinary catheter used for urine collection in females with urinary incontinence. The urinary catheter is a flexible tube used for collecting urine from bladder (102) of a critically ill patient or any individual who is not able to empty their bladder (102) on their own. Conventionally, urinary catheter comprises an inflatable balloon (110) over the peripheral surface of a flexible catheter tube (108) which together is inserted into bladder (102) via urethra (104) before inflating the balloon (110). The flexible catheter tube (108) comprises a narrow and a wide chamber such that the narrow chamber is coupled to the inflatable balloon (110) whereas the wider chamber is extended outside the inflatable balloon (110) which remains open in the bladder (102). In an example, size of the narrow chamber is similar to that of a conventional capillary tube which helps in inflating the balloon (110).

Once the catheter tube (108) is introduced into the bladder (102), the inflatable balloon (110) is then inflated by injecting air into it through the narrow chamber of the catheter tube (108). As shown in the FIG. 1A, the inflated balloon (110) of the catheter tube (108) helps in holding the urinary catheter within the bladder in a secured position. As shown in the FIG. 1B, the catheter tube (108) coming out of the bladder is coupled to a drainage bag (112) where urine is collected from the bladder directly through the wider chamber of the catheter tube (108).

FIG. 1C illustrates the urinary catheter provided with a connector coupled to the catheter tube (108). In an example, the connector comprises two sub connecting ports (114 and 116) fastened to the wider and narrow chambers of the catheter tube (108) respectively. The connecting port (114) coupled to the wider chamber of the tube (108) is then coupled to the drainage bag (112) to drain urine from bladder (102). However, there are extreme chances of getting urinary tract infections using this device as this device must be introduced into the human body.

Figure 2A:
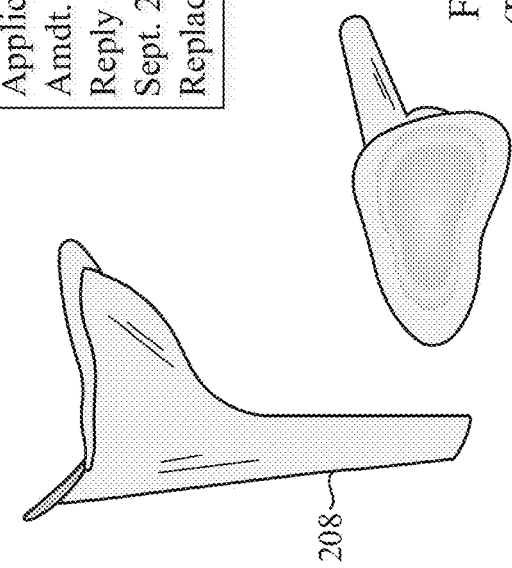
FIG. 2A through 2D are examples of external female catheters that are being used in the prior art.

FIG. 2A through 2D are examples of external female catheters that are being used in the prior art. Besides the urinary catheter which must be introduced into the human body, various external catheters are also provided to aid individuals suffering with urinary incontinence. FIG. 2A illustrates an external catheter device that entirely covers vulva region of a female. This device comprises a thin expansive material (226) at the center surrounded by an adhesive surface provided with a drain hole (204) at lower end of the device. The expansive material collects the urine which was then drained out through the drain hole (204) provided at lower end of the device. Similarly, few more devices are developed which share the functionality with a conventional diaper or under garment that helps in defecating or urinating without the use of a toilet. However, these devices remain in contact with the skin which causes irritation or rashes over the region. Further the devices are fixed externally using an adhesive which does not last for a long time.

Figure 2B:
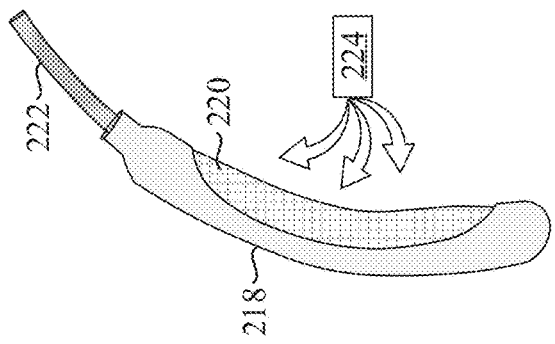

FIG. 2B illustrates another example female urination device with a funnel shape. This device needs to be held in a fixed position by an individual in such a way that the top of the device covers the vulva region so that the urine gets discharged through the funnel shaped tube (208). This device fails miserably for aiding bed ridden patients and those who are suffering with urinary incontinence as the urine discharge is involuntary.

Figure 2C:
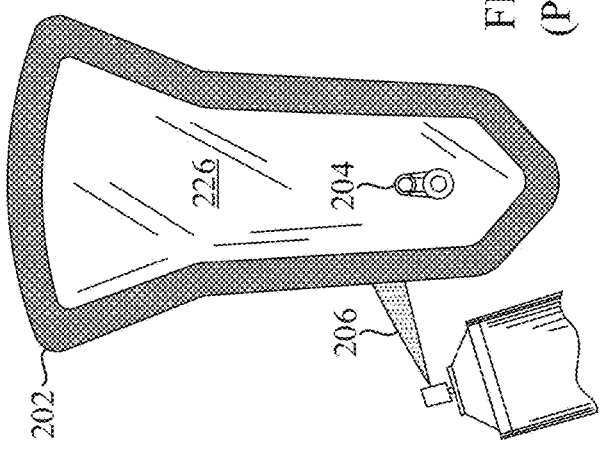

FIG. 2C is another example urine discharge device which comprises an adhesive layer/patch (212) coupled to a drainage bag (210) with an opening (214) through the patch (212). The device is configured by sticking the adhesive patch in the vulva region so that the urinal tract and vaginal opening are in place with the opening (214) of the device. The urine gets discharged through (214) and drained out through an outlet (216) provided at the bottom. This device is also not feasible as the adhesive patch often comes out of the vulva region. Further, configuring the opening (214) of the device in place with the vaginal opening and urethra is tedious and causes discomfort while using.

Figure 2D:
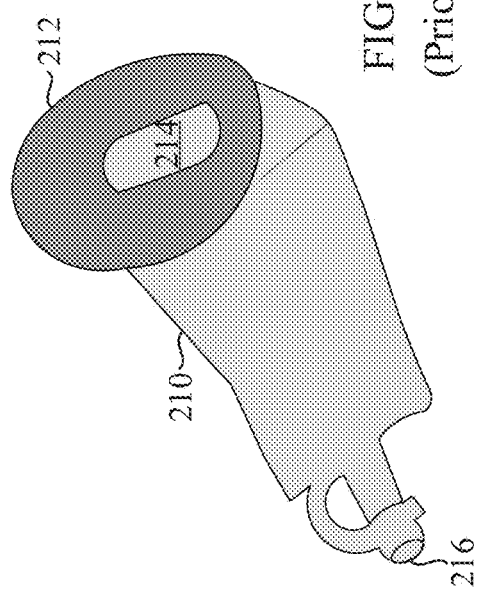

FIG. 2D is yet another example of external female catheter comprising a silicon cuff with a soft, flexible wick that helps in absorbing the urine (224) by capillary action. This device is also provided with an adhesive to place the wick of the device in the vulva region. However, all these conventional external catheters are causing discomfort while using them and are not efficient in aiding the people who are bed ridden and/or suffering with urinary incontinence. Hence, there is need for an efficient female external urine collecting device which does not cause any infection to the urinary tract or associated parts of the body.

FIGS. 3A and 3B are the diagrams illustrating the manner in which a non-invasive female urine collecting device is anchored to vaginal region in an embodiment of the present disclosure. The bladder (310) of a human body acts as a reservoir which discharges urine through urinal tract (3101) when the bladder (310) gets filled. However, weakened peripheral walls of the urinal tract (3101) at the outlet of the bladder (310) results in leakage or involuntary discharge of urine. To overcome this problem and also the aforesaid limitations offered by conventional urine collecting devices (both internal and external devices as discussed in FIG. 1 and FIG. 2A through 2D), a novel and effective female urine collecting device has been disclosed in the present disclosure.

As shown in FIG. 3A, the non-invasive female urine collecting device of the present disclosure is inserted into vaginal opening (320) in a desired position between the walls (330A and 330B) of the vagina. In an embodiment, the female urine collecting device comprises an inflatable balloon (350) surrounding a hollow cylindrical tube (340) such that the inflatable balloon (350) is covered throughout the outer surface of the tube (340) while the edges of the tube (340) remain open.

FIG. 3B illustrates a firmly configured non-invasive female urine collecting device of the present disclosure between the walls of the vagina (330A and 330B). Once the device is inserted into the vaginal region, the inflatable balloon (350) is inflated by passing air into it. In an example, the inflatable balloon (350) is provided with a separate narrow tube (360) to blow air into the balloon (350). In another example, the separate narrow tube (360) may be attached with the cylindrical hollow tube (340) forming a conventional catheter tube having two chambers.

The balloon (350) is inflated by any conventional means of blowing air into it for example, by using a syringe. The inflated balloon pushes the walls (330A and 330B) of the vagina away to hold the vaginal opening rigidly. This makes the inner hollow cylindrical tube (340) to act as a temporary vaginal opening.

Figure 3D:
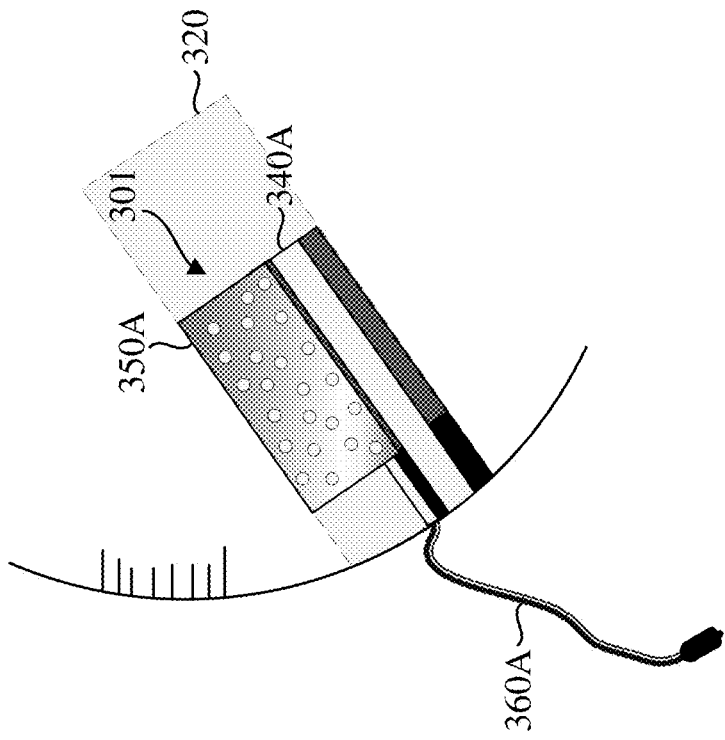
FIGS. 3C and 3D are the diagrams illustrating anchoring of the non-invasive female urine collecting device to vaginal region in another embodiment of the present disclosure.
Figure 3C:
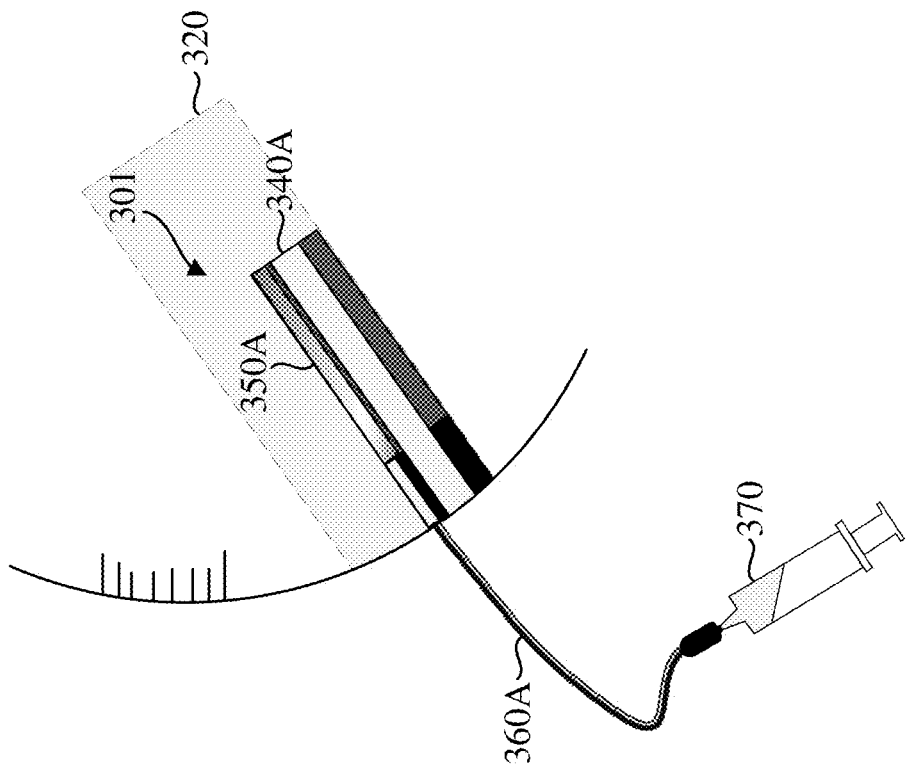

FIGS. 3C and 3D are the diagrams illustrating anchoring of the non-invasive female urine collecting device to vaginal region in another embodiment of the present disclosure. FIG. 3C illustrates the female urine collecting device (301) positioned within the vaginal opening (320) before configuring it in another embodiment. In the present embodiment, the device (301) comprises an inflatable balloon (350A) only on one side of the hollow cylindrical tube (340A). The balloon (350A) is then inflated by blowing air into it through the tube (360A) using a syringe (370). In an embodiment, the inflatable balloon (320) is elastic in nature and comprises a synthetic material which makes the balloon more durable. This inflated balloon pushes the walls of the vaginal opening away from each other and holds the region firmly. The device (301) with the inflated balloon (350A) on one side is shown in FIG. 3D.

Figure 4B:
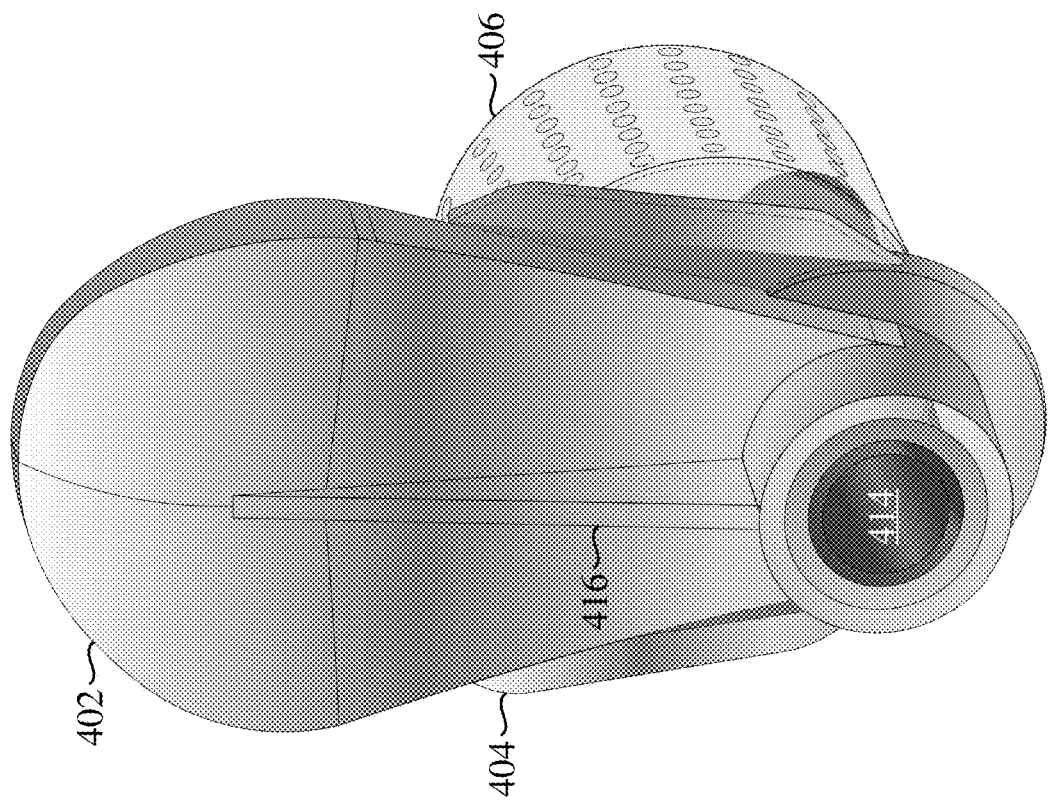
FIGS. 4A and 4B are the diagrams illustrating the non-invasive female urine collecting device of the present disclosure.
Figure 4A:
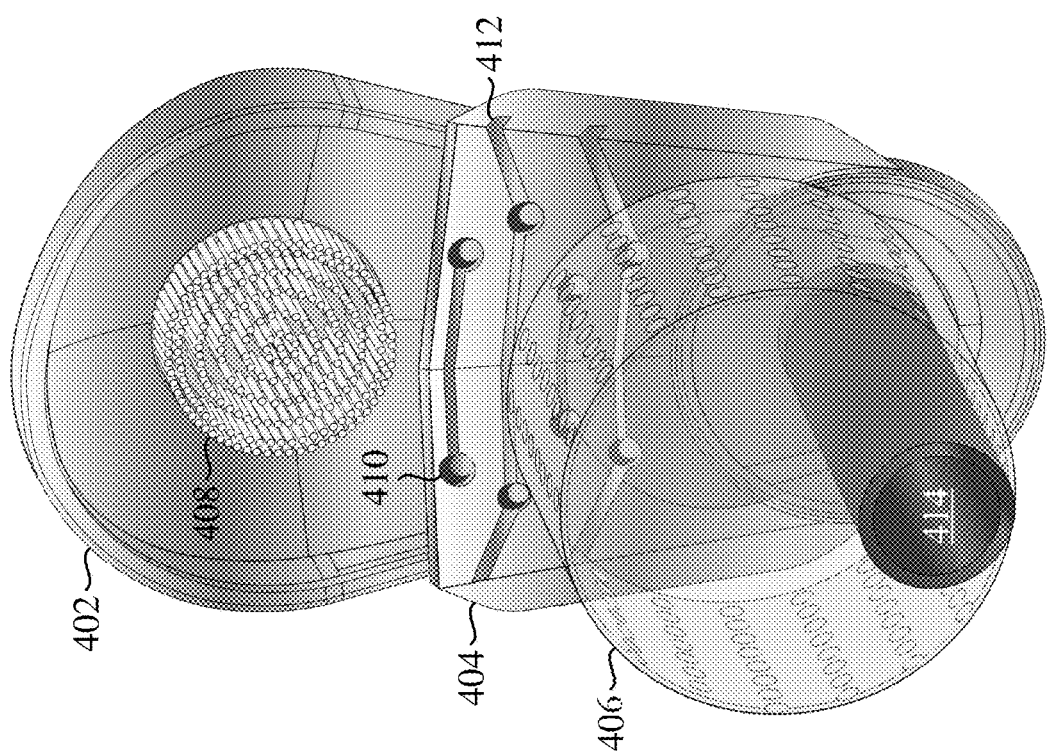

FIGS. 4A and 4B are the diagrams illustrating the non-invasive female urine collecting device of the present disclosure. The non-invasive female urine collecting device comprises a urine collection member with a first membrane (hereafter referred to as a primary unit) (402) and a second membrane (hereafter referred to as a secondary unit) (404), an inflatable balloon (406), a first pipe (hereafter referred to as a hollow cylindrical tube) (414) and a supporting spine (416).

The primary unit (402) is an elongated and inclined cup like structure (as shown in FIGS. 4A and 4B) comprising a set of spikes (408) in its inner surface. The primary unit (402) discharges urine that is coming directly from the urinal tract when the device is configured into vaginal opening of an individual. In an embodiment, the primary unit (402) is made up of medical grade silicon but not limited to an elastomeric material for example, rubber, plastic and the like. The set of spikes (408) may be arranged in various patterns in different shapes, sizes and area within the inner surface of the primary unit (402).

The secondary unit (404) is a flat plate like structure that is assembled on top of the primary unit (402) just below the set of spikes together constituting a hollow space between them. In an example, length of the secondary unit (404) is half to that of the length of the primary unit (402). The secondary unit (404) guides the overflow of urine that is coming from the urinal tract through the primary unit (402) into the hollow chamber formed between the primary and secondary unit (402 and 404). The secondary unit (404) comprises plurality of vent holes (410) that are interconnected through guiding pathway of grooves (412) to guide the flow of urine into the vent holes (410). In an embodiment, the secondary unit (404) is also made up of medical grade silicon but not limited to an elastomeric material for example, rubber, plastic and the like.

The inflatable balloon (406) is a transparent silicon elastomeric material that is coupled on top of the hollow cylindrical tube (414) in such a way that the inflatable balloon (406) gets inflated around the cylindrical tube (414) on its outer surface. In an embodiment, an air injecting hole is provided on the cylindrical tube (414) to inject air to inflate the inflatable balloon (406) to hold the device firmly in place. In an example, the cylindrical tube (414) is a flexible tube with both ends remain opened passing through lower end of the secondary unit (404) as shown in the figures in such a way that the inflatable balloon (406) remains on anterior side of the device (as shown in the FIG. 4A). The supporting spine (416) is a structure provided on posterior side of the primary unit in the middle which acts as a midrib to the primary unit (402) (as shown in the FIG. 4B) providing mechanical strength to the device.

FIG. 5A through 5C are the diagrams illustrating anti-splash cone spikes present in the non-invasive female urine collecting device of the present disclosure. The primary unit (502) of the device comprises a set of spikes (506) protruding outside from inner surface of the primary unit (502). These spikes collect and discharge urine that is gushing towards it from the urinal tract by passing it to downstream behind the secondary unit (504). The spikes (506) of the device acts as an anti-splash shield which entraps the urine within them to pass through downstream flow. FIGS. 5B and 5C illustrates the usage of spikes (506) on inner walls of the primary unit (502) as an anti-splash layer. As shown in FIG. 5B, the primary unit (502) without the spikes on its inner walls comprises a planar surface (510) throughout the inner surface. When the urine (508) starts running onto its surface, the urine (508) gets splashed from the planar surface (510) and scatters in its surroundings. This causes discomfort while using the device. Hence, a set of cone shaped spikes in different patterns (only circular pattern is shown in 506) are provided on the inner surface of the primary unit (502). This cone shaped spikes (512) entraps the urine (508) running towards it within the spikes as shown in FIG. 5C and reduces the velocity at which the urine (508) is running out from the urinal tract which makes them operable as anti-splash shield.

Figure 6A:
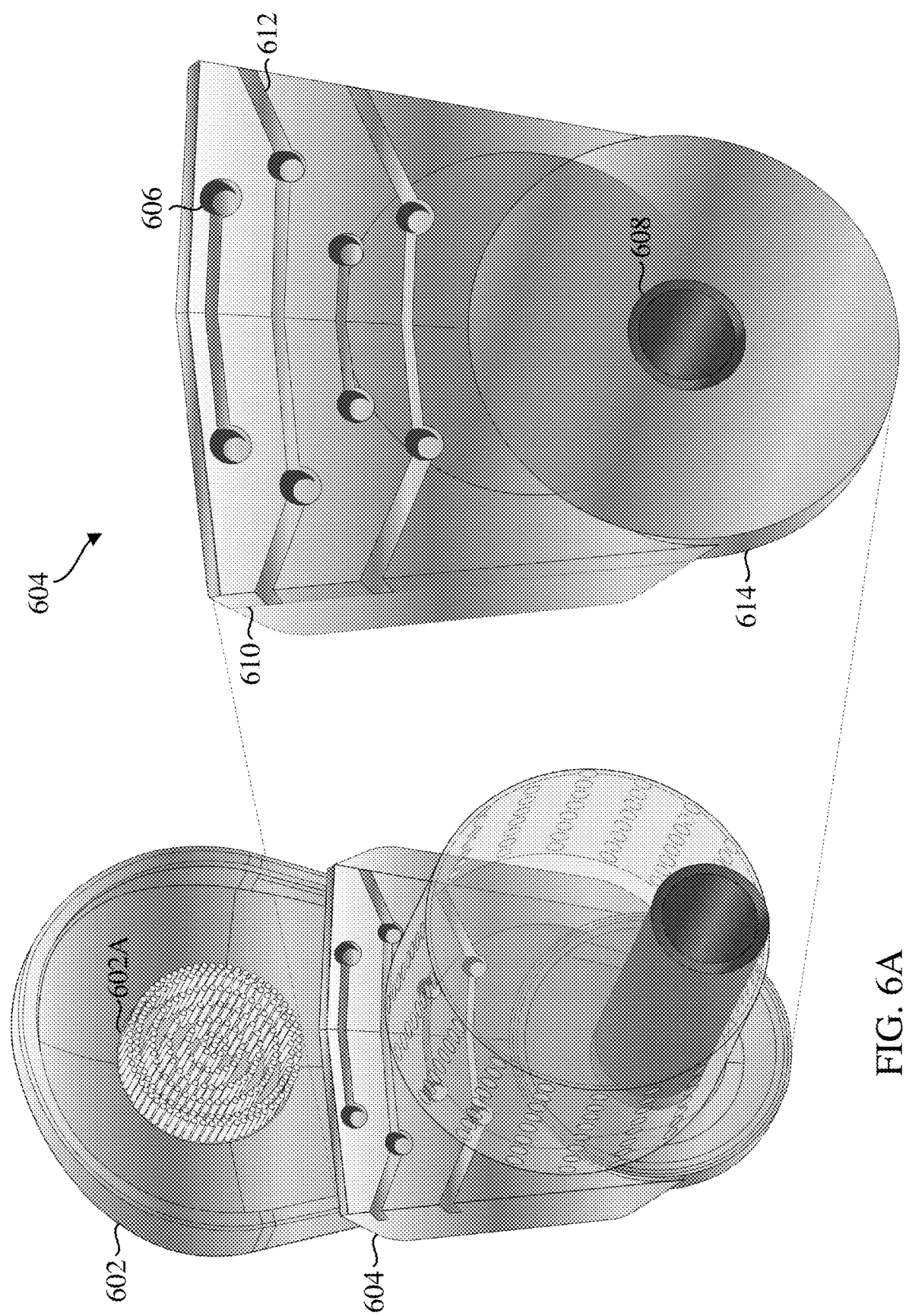
FIGS. 6A and 6B are the diagrams illustrating vent holes of the non-invasive female urine collecting device of the present disclosure.
Figure 6B:
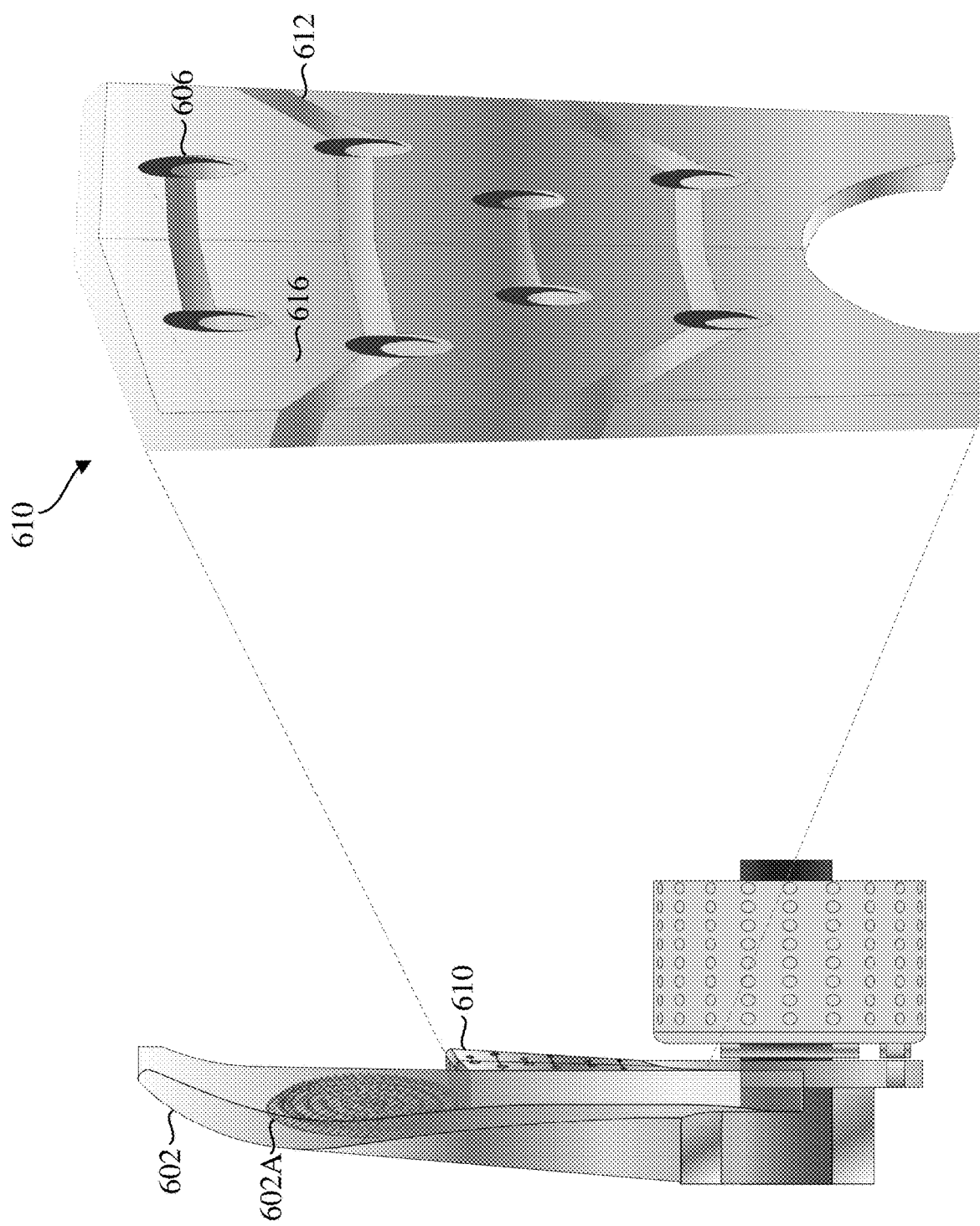

FIGS. 6A and 6B are the diagrams illustrating vent holes of the non-invasive female urine collecting device of the present disclosure. As discussed in the previous embodiments, the female urine collecting device of the present disclosure comprises the primary unit (602) and the secondary unit (604) assembled together as shown. The primary unit (602) comprises a set of anti-splash spike shield (602A) which guides the flow of urine downwards behind the secondary unit 604. However, the urine coming out from the urinal tract may hit the anti-splash shield at high velocity which leads to overflow or leakage from the shield onto the secondary unit (604). Therefore, the secondary unit is provided with plurality of vent holes (606) which are interconnected to each other by plurality of guiding pathway grooves (612) as shown in the FIG. 6A. In an embodiment, the secondary unit comprises two sub units in which the first subunit (610) comprises the plurality of vent holes (606) and the grooves (612) while the second subunit (614) comprises a circular opening (608) to accommodate the hollow cylindrical tube with inflatable balloon of the device to pass through it.

FIG. 6B illustrates the first subunit (610) of the secondary unit (604) with plurality of vent holes and grooves to guide the overflowed urine into the downstream flow of urine coming from the primary unit (602). As shown there, the primary unit (602) and the secondary unit (604) together forms a urine collection pouch for the downstream flow. As shown there, the first subunit (610) comprises plurality of vent holes (606) that run through the secondary unit in such a way that each vent hole is extended from anterior side to posterior side at 30° angle downwards the planar surface of the secondary unit. The extended hole at 30° angle inwards is represented in the figure as (616). In an embodiment, the vent holes (606) are provided with inclination towards the edges of the first subunit (610) in such a way that the central longitudinal region of the first subunit (610) is at the higher planar region when compared to the vent holes (606). This allows the flow of urine into the vent holes (606) through the guiding grooves (612). The grooves (612) are also made thick and with inclination at an angle of 30° inwards similar to that of the vent holes. These grooves (612) channel the overflowed urine throughout their path to the vent holes which are inclined and/or below the planar surface of the central longitudinal region of the first subunit (610).

FIGS. 7A and 7B are the diagrams illustrating functionality of the non-invasive female urine collecting device in collecting urine from urethra in an embodiment of the present disclosure. FIG. 7A illustrates the manner in which the urine is collected from the device in an embodiment. Once the urine is coming from the urinal tract of urethra, it first strikes the anti-splash shield (704) of the primary unit (702). There it gets entrapped within the cone-shaped spikes of the anti-splash shield (704) and starts discharging downwards at reduced velocity into a reservoir (708) of the device.

Further, the higher rate of velocity at which the urine coming towards the anti-splash shield (704) leads to overflowing or leakage of few drops of urine (710) onto the secondary unit (714) of the device. The secondary unit (714) comprising vent holes (718) that run through the first subunit are interconnected by grooves (716). These guide the overflowed drops of urine (710) into the downstream flow (706) coming from the anti-splash shield (704) of the primary unit (702) behind the secondary unit (714).

FIG. 7B illustrates the manner in which the vent holes (718) and grooves (716) guides the overflowed urine into the downstream flow (706) behind the secondary unit (714). As shown there, the overflowed urine gets inside the grooves (716) and follows their path to reach the vent holes (718) which are inclined and located in the inner planar surface of the secondary unit. The vent holes which are made at an angle of 30° collect the overflowed urine through the grooves and passes it to flow inwards behind the secondary unit to join the downstream flow (706). The downstream flow of urine gets collected (708 as shown in the FIG. 7A) in the reservoir (708) which is sent outside through an outlet pipe provided to it. Thus, the urine from urethra is collected from the female urine collecting device of the present disclosure.

Figure 7C:
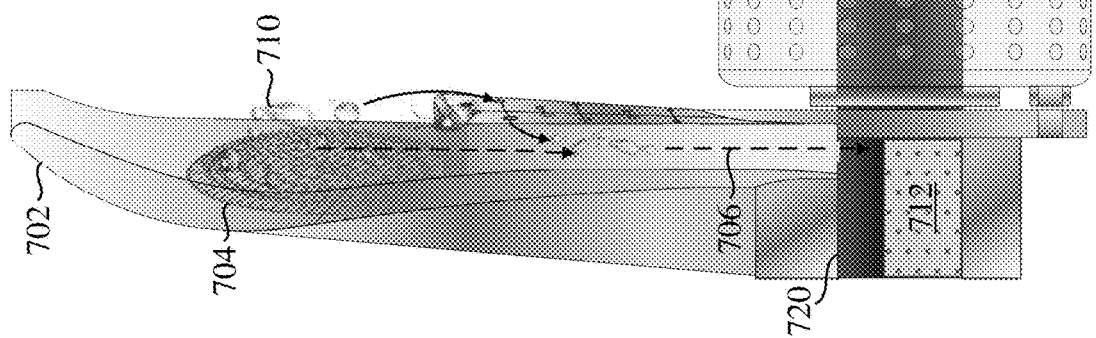
FIG. 7C is a diagram illustrating the collection of urine from the primary unit and secondary unit of the device in another embodiment of the present disclosure.

FIG. 7C is a diagram illustrating the collection of urine from the primary unit and secondary unit of the device in another embodiment of the present disclosure. In another embodiment, the urine coming from the anti-splash shield (704) of the primary unit (702) gets discharged downwards at reduced velocity. This downstream flow (706) of urine then enters into the cylindrical hollow tube/pipe (720) of the device which passes through the second subunit of the secondary unit (714). Further, a valve mechanism may be implemented to avoid flow of the urine back into the cylindrical tube (720) which acts as the temporary vaginal opening.

Figure 8A:
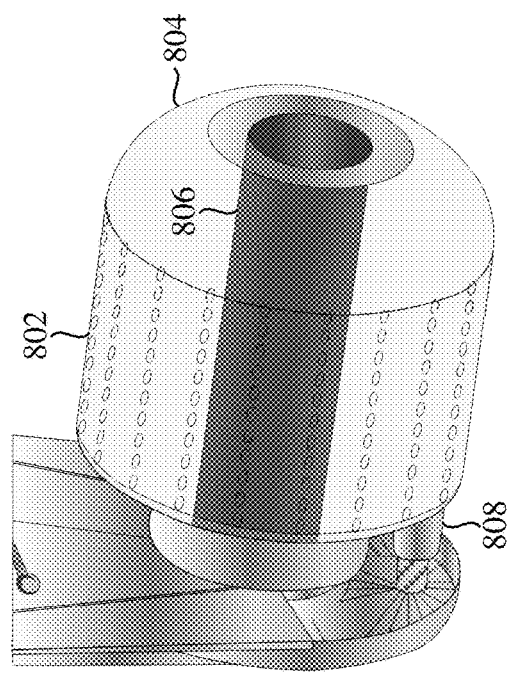
FIGS. 8A and 8B are the diagrams illustrating the air inflatable balloon coupled with an anchoring support of the non-invasive female urine collecting device of the present disclosure.
Figure 8B:
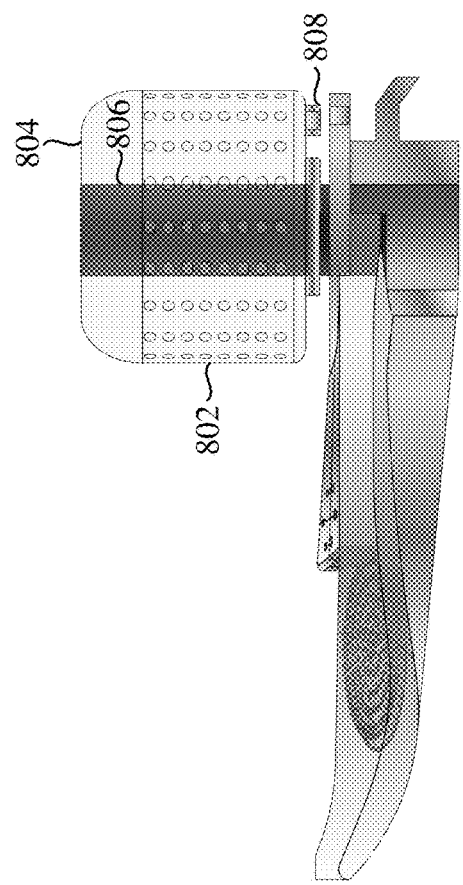

FIGS. 8A and 8B are the diagrams illustrating the air inflatable balloon coupled with an anchoring support of the non-invasive female urine collecting device of the present disclosure. The inflatable balloon (802) is configured on top of the cylindrical tube (806) which surrounds the entire peripheral surface of the tube (806) on the anterior side of the device. In an embodiment, the inflatable balloon comprises a dotted pattern silicon material of medical grade which may be sterilized before using the device. Further, the inflatable balloon (802) is provided with an anchoring support (804) that holds the inflated balloon in a firm position with the cylindrical tube (806) at its center as shown. The inflatable balloon is inflated by blowing air into it through a non-return valve (808) by using a syringe or other conventional blowing mechanism. In an embodiment, the balloon (802) is blown after placing the device into vaginal opening of an individual. Then the balloon (802) starts inflating and pushes the walls of the vaginal opening away and helps in holding the device firmly in the desired position.

FIG. 9 illustrates an example implementation of the non-invasive female urine collecting device of the present disclosure while in coma/supine condition in an embodiment. The female urine collecting device (902) is configured within the vaginal opening of an individual (as discussed in the FIGS. 3A and 3B) by inflating the balloon of the device against the walls of vagina in such a way that the primary unit of the device comprising the anti-splash shield covers the opening of urinal tract (urethra) coming from the bladder. This device may be configured to those individuals who are bed ridden in coma/supine condition but not limited to those who are facing urinary incontinence problem. Once the device is configured, the cylindrical tube that is coming out of the secondary unit of the device is coupled to a drainage bag (910) using a conventional flexible tube (908). In an embodiment, conventional catheter tube comprising two separate chambers throughout the length that is used to collect vaginal secretion as well as urine from the device. And a separate tube with one end connected to the inflatable balloon and another end coupled with a non-return valve is used for blowing air. Urine gets released from the bladder (906) when it gets filled and is passed through the urinal tract and reaches the anti-splash shield of the primary unit of the device (902). From the primary unit it enters the downstream flow and passes into the drainage bag (910) through the tube (908) coupled to it. Also, the overflowed urine from the primary unit enters the grooves of the secondary unit and joins the downstream flow to enter the drainage bag (910) as discussed in the FIGS. 7A through 7C.

FIG. 10 is a sketch illustrating a urinary drainage bag coupled to the non-invasive female urine collecting device of the present disclosure for collecting urine and vaginal secretions in another embodiment. Once the device (1001) is plugged into the vaginal opening by inflating the balloon (1004), the primary unit (1002) of the device (1001) collects urine from the urethra and passes it to outlet (1008) of the reservoir. Also, the hollow cylindrical tube (1006) of the device collects the vaginal secretions from the vaginal opening and delivers outside from its opening on the posterior side of the device (1001). In an embodiment, a conventional catheter tube (1010) comprising two chambers with two connectors (1010A and 1010B) is used to collect the urine as well as vaginal secretions from the outlet (1008) of reservoir and the cylindrical tube (1006) respectively.

In yet another embodiment, the device (1001) which collects the urine through the cylindrical pipe (1006) as discussed in the FIG. 7C requires only a single tube (1010) instead of two connectors to collect the urine and vaginal secretions. This tube (1010) is then coupled to a detachable drainage bag (1012) which collects the urine and vaginal secretions from the device (1001). In an example, the drainage bag (1012) is provided with a couple of Velcro straps to hold the legs/thighs or any other body part of the individual.

Figure 11A:
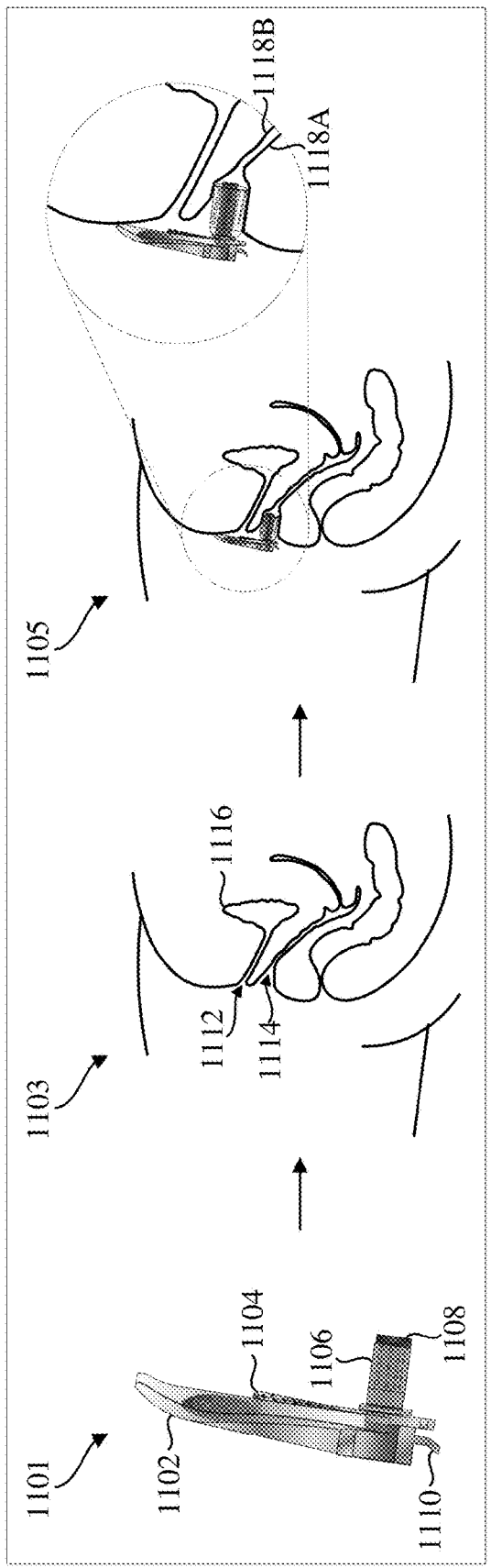
FIGS. 11A and 11B are the sketches illustrating the installation of the non-invasive female urine collecting device facilitating comfortable anatomical fitting in an embodiment.
Figure 11B:
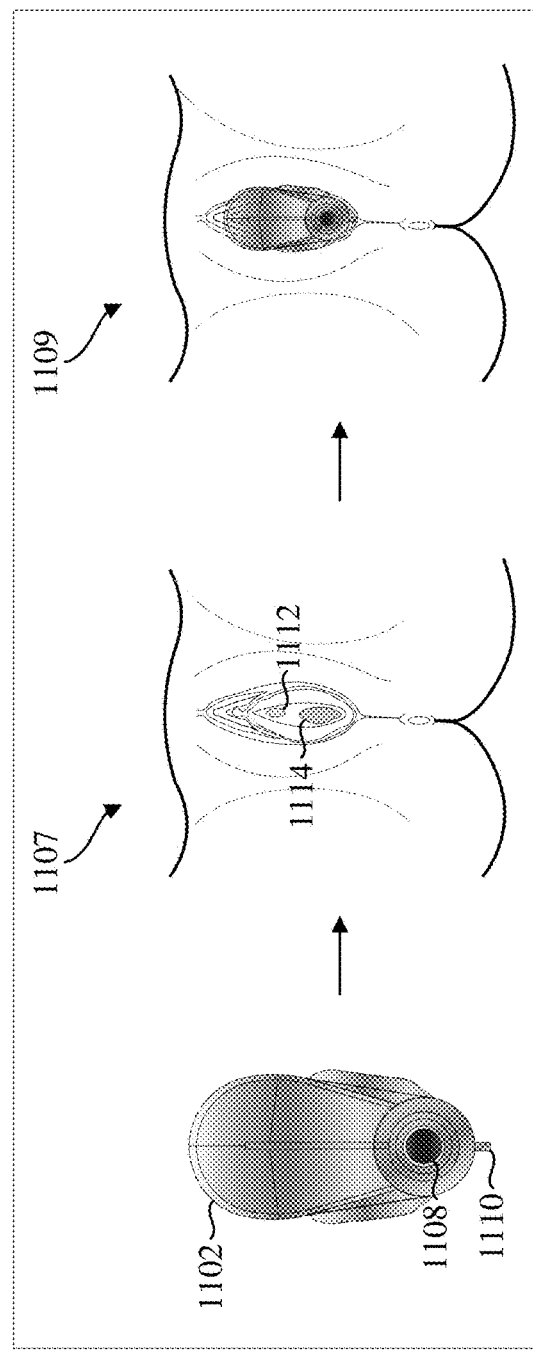

FIGS. 11A and 11B are the sketches illustrating the installation of the non-invasive female urine collecting device facilitating comfortable anatomical fitting in an embodiment. FIG. 11A illustrates side view of vaginal opening while configuring the female urine collecting device of the present disclosure. As shown there, (1101) shows the female urine collecting device of the present disclosure comprising the primary unit (1102), the secondary unit (1104), the cylindrical tube (1108), the inflatable balloon (1106) and the outlet (1110) for discharging the urine. The device (1101) in its initial position without inflating the balloon (1106) is placed into the vaginal opening (1114) of an individual. The inflatable balloon is then inflated by passing air into it which pushes the side walls of vagina (1118A and 1118B) and holds the vaginal opening firmly as shown in the FIG. 1105). As there is not internal contact of the device with urinal tract or bladder, there is negligible chance of getting urinal tract infections using this device. Further, the device causes negligible damage to the associated organs such as swelling, widening of wall openings or irritations in the device associated regions. Calibrating/fixing the device (1101) only pushes the vagina side walls away from each other to get hold of the vaginal opening and causes no anatomical changes in the human body. FIG. 11B illustrates the front view of the device as well as the vaginal opening while configuring the female urine collecting device. As shown there, front view (1107) of the device (1101) illustrates the primary unit (1120), the cylindrical tube (1122) and the outlet (1124) for discharging urine from the device. The anatomy of the vulva (front view) is shown (as in 1109) comprising a vaginal opening (1126) and urethra (1128) connected to the bladder. The cylindrical tube (1122) is then inserted into the vaginal opening and calibrated/fixed by using the inflatable balloon as discussed in the FIG. 11A. Thus, the device (1101) holds the vaginal opening with the primary unit (1120) having the anti-splash shield as shown (as in 1111) in a position by covering the urethra (1128) to collect the urine.

Figure 12C:
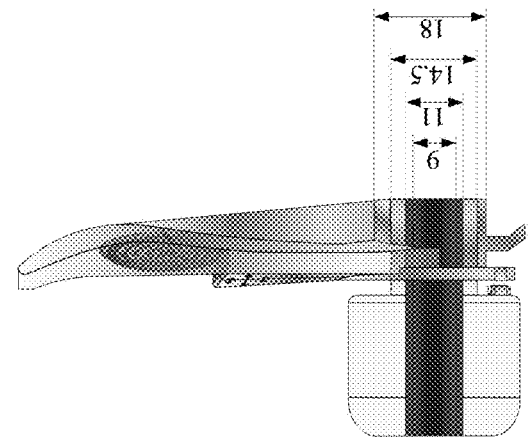
FIG. 12A through 12E are the diagrams illustrating compactness of the non-invasive female urine collecting device of the present disclosure with measurements in three-dimensional axis.
Figure 12B:
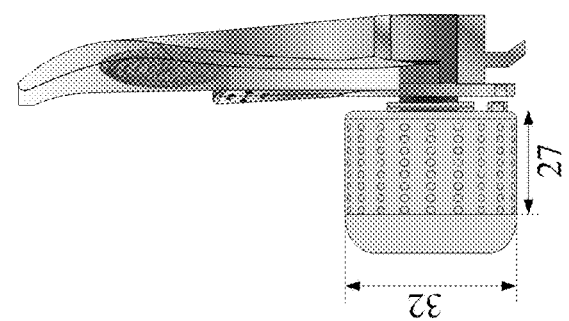
Figure 12A:
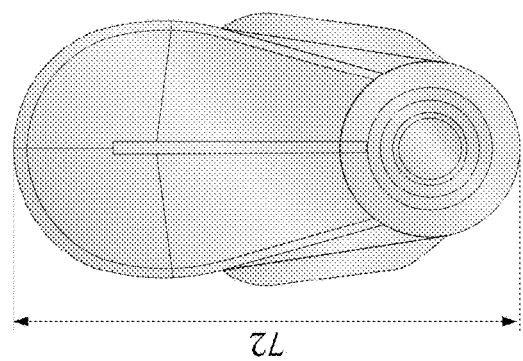
Figure 12E:
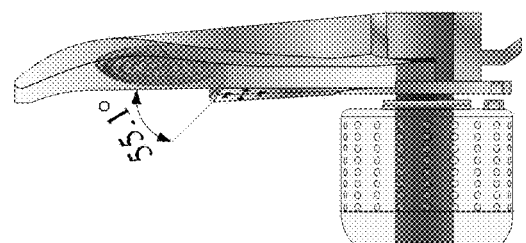
Figure 12D:
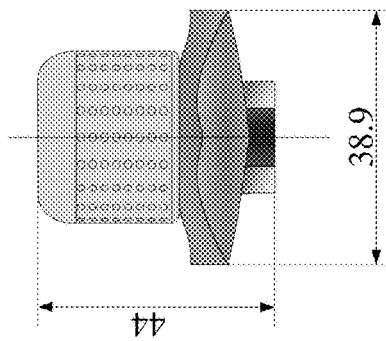

FIG. 12A through 12E are the diagrams illustrating compactness of the non-invasive female urine collecting device of the present disclosure with measurements in three-dimensional axis on a scale of 5:1. FIG. 12A represents front view of the device in which the length of the entire device is determined as 72 mm from the tip of the primary unit to end of the secondary unit as shown. FIG. 12B illustrates that the length of the inflatable balloon is around 30 mm and the diameter of inflatable balloon is adjustable from 22 mm to 45 mm diameter. FIG. 12C illustrates that inner diameter of the cylindrical tube which is 9 mm whereas outer diameter is 11 mm. Further it represents that inner diameter of the reservoir is 14.5 mm whereas the outer diameter is 18 mm respectively. FIG. 12D represents top view of the device wherein the length and width of the device are determined as 44 mm and 38.9 mm respectively. FIG. 12E illustrates the angle between the primary unit (from the surface of anti-splash shield) and the secondary unit to be 55.1° with the vent holes made at 30° angle within the secondary unit of the device.

While various embodiments of the present disclosure have been described above, it should be understood that they have been presented by way of example only, and not limitation. Thus, the breadth and scope of the present disclosure should not be limited by any of the above-discussed embodiments but should be defined only in accordance with the following claims and their equivalents.

What is claimed is:

1. A non-invasive female urine collection device comprising:
   a first pipe, in that an inflatable balloon is attached to a first end of the first pipe; and
   a urine collection member comprising a first membrane that is elongated and curved to form a cup on its upper part, a set of spikes formed on the upper part of the first membrane within the cup, and a second membrane that is shorter than the first membrane is attached to the first membrane forming a urine collection pouch on its lower part, the urine collection member is attached to a second end of the first pipe such that, when the first end of the first pipe is inserted into a vagina, the cup covers a urethra and the set of spikes come axially in line with the urethra,
   wherein the urine from urethra is received on the set of spike preventing splashing and allowing the urine to flow from upper part to the urine collection pouch on the lower part of the first membrane.

2. The non-invasive female urine collection device of claim 1, wherein the second membrane further comprising a plurality of vent holes and a plurality of grooves coupled to the plurality of vent holes, wherein the grooves are formed on the outer surface of the second membrane such that urine spilled on the outer surface of the second membrane is directed back into the urine collection pouch through the plurality vent holes.

3. The non-invasive female urine collection device of claim 2, wherein the plurality of vent holes are extended from anterior side to posterior side of the second membrane at 30° angle sloping into the urine collecting pouch.

4. The non-invasive female urine collection device of claim 3, wherein the first membrane further comprising a supporting spine extending from the lower part to the upper part on back side of the cup so that, the first membrane is held perpendicular and pivoted to the first pipe.

5. The non-invasive female urine collection device of claim 4, further comprising an outlet pipe coupled to urine collection pouch to drain the urine collected within the urine collection pouch.

6. The non-invasive female urine collection device of claim 5, further comprising an air injecting hole formed on the first pipe to inject air to inflate the inflatable balloon to hold the device firmly in place.

7. The non-invasive female urine collection device of claim 6, wherein the urine collection member comprises of a medical grade silicon but not limited to an elastomeric material like rubber and plastic.

* * * * *